United States Patent [19]

Dowd et al.

[11] Patent Number: 4,973,601

[45] Date of Patent: Nov. 27, 1990

[54] CONTROL OF INSECTS BY FUNGAL TREMORGENIC MYCOTOXINS

[75] Inventors: Patrick F. Dowd, Peoria, Ill.; Richard J. Cole, Albany, Ga.; Ronald F. Vesonder, Peoria, Ill.

[73] Assignee: The United States of America, as represented by the Secretary of Agriculture, Washington, D.C.

[21] Appl. No.: 201,143

[22] Filed: Jun. 1, 1988

[51] Int. Cl.$^5$ ...................... A01N 43/38; A01N 43/16

[52] U.S. Cl. .................................... 514/410; 514/411; 514/415; 514/453; 514/463; 424/DIG. 8

[58] Field of Search ............... 514/453, 458, 410, 411, 514/415; 424/DIG. 8

[56] References Cited

PUBLICATIONS

Takao Yokota et al., "Isolation and $^{13}C$ NMR Study of Cyclopyazonic Acid, A Toxic Alkaloid Produced by Muscardine Fungi *Aspergillus flavus* and *A. oryzae,*" Agric. Biol. Chem. 45(1): 53–56, (1981).

Chem. Abst. 104:124549d, 1986.

Chem. Abst. 87:146755t, 1977.

Chem. Abst. 84:26635v, 1976.

Chem. Abst. 87:50473y, 1977.

Chem. Abst. 97:69756w, 1982.

Chem. Abst. 86:153838e, 1977.

Chem. Absts. 110:54201z & 110:228896x, 1989.

*Primary Examiner*—John W. Rollins

*Attorney, Agent, or Firm*—M. Howard Silverstein; John D. Fado; Curtis P. Ribando

[57] ABSTRACT

Tremorgenic mycotoxins produced by fungi in the genera Penicillium, Aspergillus, and Claviceps have been found to have potent insecticidal and growth inhibitory activity against the corn earworm and the fall armyworm. Penitrem A and dihydroxyaflavinine are most effective.

12 Claims, No Drawings

CONTROL OF INSECTS BY FUNGAL TREMORGENIC MYCOTOXINS

BACKGROUND OF THE INVENTION

Mycotoxins and other fungal metabolites are thought to serve as chemical defense systems for the fungi that produce them, and may also be of use in protecting the food source from consumption by other organisms [see: D. T. Wicklow, "Ecological Approaches to the Study of Mycotoxigenic Fungi" In Toxigenic Fungi-Their Toxins and Health Hazards, H. Korata et al. (ed.), Elsevier, New York, pp. 78-86, (1984)].

The fungal tremorgenic mycotoxins, a group of metabolites capable of eliciting tremors in vertebrate animals, are produced by fungi that infect field crops such as corn, oats, and barley [K. M. Domsch et al., Compendium of Soil Fungi, Vol. I, Academic Press, New York (1979)]. These crops may also be infested by the corn earworm, *Heliothis zea* and the fall armyworm, *Spodoptera frugiperda* [see: C. L. Metcalf et al., Destructive and Useful Insects, McGraw-Hill, New York (1962)].

Approximately 50 fungal tremorgenic mycotoxins have been described and may be divided into several subgroups based on chemical similarity; including the penitrem group, the fumitremorgin-verruculogen group, the paspalitrem group, the tryploquivaline group, and the tetramic acid group. All of these tremorgens have the indole moiety of tryptophan in common.

Tremorgenic mycotoxins are produced by such fungi as the genera Penicillium, Aspergillus, and Claviceps [see: R. J. Cole and R. H. Cox, "Tremorgen Group," Handbook of Toxic Fungal Metabolites, Academic Press, New York, p. 355 (1981)].

Other classes of fungal mycotoxins such as aflatoxins and trichothecenes have been reported to be toxic to insects as have certain cyclic peptides produced by microorganisms including the piericidins and destruxins [see: V. F. Wright et al., "Mycotoxins and Other Fungal Metabolites as Insecticides," In Microbial and Viral Pesticides, E. Kurstak (ed.), Marcel Dekker, New York, pp. 559-583 (1982); S. Tamura et al., "Destruxins and Piericidins," In Naturally Occurring Insecticides, M. Jacobsen et al. (eds.), Marcel Dekker, New York, pp. 499-539 (1971); T. Robinson, "The Evolutionary Ecology of Alkaloids," In Herbivores: Their Interaction With Secondary Plant Metabolites, G. A. Rosenthal et al. (eds)., Academic Press, New York, pp. 413-448 (1979)]. Lolitrem neurotoxins which occur in ryegrass have the indole moiety in their chemical structure. The biosynthetic origin of these materials is not known. Lolitrem B has been shown to be toxic to the Argentine stem weevil [Prestidge et al., Chem. Abst. 103:279 (1985)]. However, the fungal tremorgens are a group of mycotoxins that has not been previously evaluated for toxicity to insects.

SUMMARY OF THE INVENTION

We have now discovered that the class of fungal metabolites known as tremorgenic mycotoxins which contain the indole moiety is toxic to insect species. Specific members of this class found to possess insecticidal activity include: penitrem A, verruculogen, dihydroxyaflavinine, cytochalasin H, paspaline, paxilline, chaetoglobosin C, and cyclopiazonic acid.

In accordance with this discovery, it is an object of the invention to define a previously unrecognized class of pest control agents having potential availability from both biological and synthetic sources.

It is also an object of the invention to provide a new and unobvious use for fungal tremorgenic mycotoxins.

Other objects and advantages of this invention will become readily apparent from the ensuing description.

DETAILED DESCRIPTION OF THE INVENTION

Members of the group of tremorgenic mycotoxins were isolated from fungal sources by procedures previously described in the literature, or purchased from commercial sources.

Penetrem A was isolated from *Penicillum sp.* by the procedure of Malaryandi et al. [J. Environ. Sci. Health B11(2): 139-164 (1976)]. Its structure is shown below:

Verruculogen was isolated by the procedure of Fayos et al. [J. Am. Chem. Soc. 96:6785-6787 (1974)]. The structure is as shown below:

Dihydroxyaflavinine was isolated from *Aspergillus flavus* by the procedure of Cole et al. [J. Agric. Food Chem. 29:293-295 (1981)]. The structure is as shown below:

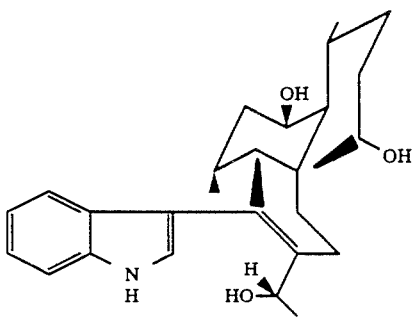

Cytochalasin H was isolated from *Phomopsis sp.* by the procedure of Wells et al. [Can. J. Micro. 22:1137–1143 (1976)]. It has the following structure:

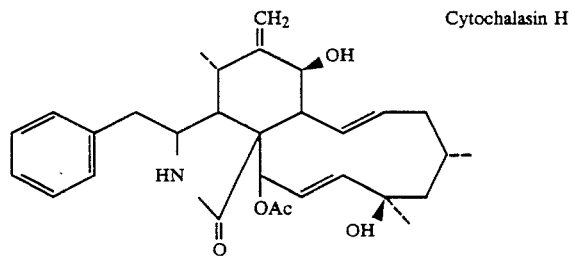

Cytochalasin H

Paspaline was isolated by the procedure of Cole et al. from *Claviceps paspali* [J. Agric. Food Chem. 25:1197–1201 (1977)]. The structure is as shown below:

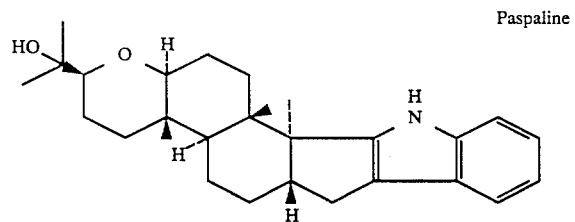

Paspaline

Paxilline was isolated by the procedure of Cole et al. from *Penicillium paxilli* [Can. J. Micro. 20:1159–1162 (1974)]. The structure is shown below:

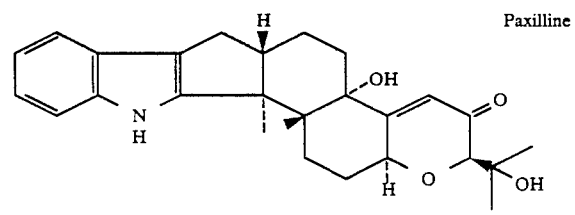

Paxilline

Chaetoglobosin C and cyclopiazonic acid were purchased from Sigma Chemical Company, St. Louis, MO.

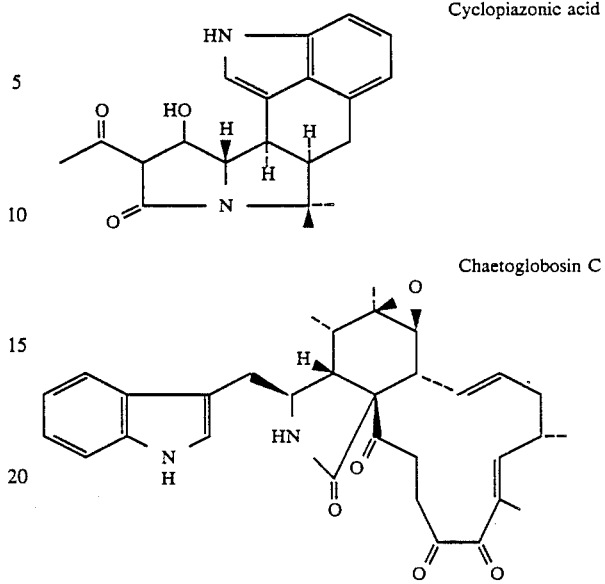

Pure materials were tested against insects as described in Example 2.

As a practical matter, it is envisioned that commercial formulations of the subject pesticidal agents would be prepared directly from fungal extracts, or fractions derived from such extracts, thereby obviating the need to isolate the compounds in pure form. It is clear from a typical fractionation scheme, presented in Example 1 for dihydroxyaflavinine, that the tremorgenic mycotoxins are soluble in chloroform, ethyl ether, and ethyl acetate. Other suitable solvents could be readily determined by the skilled artisan. Of course, for applications demanding a high degree of specificity, that is, a high level of predictability of the intended response by both target and nontarget organisms, it would normally be preferred to prepare the formulations from pure or substantially pure tremorgens. For example, it is possible that extraneous substances in the natural fungal material would have an undesirable masking or antagonist effect in regard to the intended activity, or a toxic effect toward the nontarget species. These same considerations of purity would be applied to compounds produced synthetically.

The potency of these agents dictates that they be applied in conjunction with a suitable inert carrier or vehicle as known in the art. Of particular interest are those which are agronomically acceptable. Alcohols, ketones, esters, and aqueous surfactant mixtures are illustrative of suitable carriers. Depending on the substrate, target species, mode of application, and type of response desired, the concentration of active ingredient in the final composition may vary considerably, but typically should be at least about 1 ppm. Factors such as phytotoxicity toward the treated plant and tolerance of non-target species can be used by the skilled artisan in determining the maximum level.

Depending on the pest species, concentration of agent, and method of application, the subject tremorgens act to control pests by one or more mechanisms, including, for instance, death inducement, growth regulation, or sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or "pesticidally effective amount" is defined to mean those quantities of agent which will result in a significant mortality rate of a test group as compared to an untreated group. The actual effective amount may vary with the species of pest, stage of larval development, the nature of the substrate, the particular tremorgenic agent, the type of vehicle or carrier, the period of treatment, and other related factors.

To be effective, the agent must be applied to the locus of, or the vicinity of, the pest to be controlled. When the agent is intended as a stomach poison, it is applied in conjunction with its carrier to the pest diet. In the case of plants, the composition will typically be applied to the leaf surfaces or else systemically incorporated. Alternatively, when the agent is to be used as a contact poison, any method of topical application, such as direct spraying on the pest or on a substrate which is likely to be contacted by the pest, would be appropriate.

The tremorgenic compounds encompassed herein are effective in controlling a variety of multicellular organisms. Without desiring to be limited thereto, pests of particular interest known to be vulnerable to treatment are agronomically important insects, especially those of the order Lepidoptera. It can be seen from the results of evaluation as reported in Table I that penitrem A is the most active growth inhibiting material for *H. zea* while verruculogen is the most effective for *S. frugiperda*. Greatest mortality of *S. frugiperda* is achieved by treatment with dihydroxyaflavinine.

The following examples are intended only to further illustrate the invention and are not intended to limit the scope of the invention which is defined by the claims.

Example 1

Isolation of dihydoxyaflavinine [R. J. Cole et al., J. Agric. Food. Chem. 29:293-295 (1981)].*A. flavus* (NRRL 3251) isolate was obtained from the ARS Culture Collection, Peoria, IL. The fungus was mass-cultured in 2.8 L Fernbach flasks each containing 100 g of shredded wheat supplemented with 200 ml of Difco mycological broth (pH 4.8) plus YES medium [N. D. Davis et al., Appl. Microbiol. 14:378 (1966)].

After being grown for 2 weeks at 26°-29° C., the cultures were extracted with hot chloroform. The crude chloroform extract was chromatographed on a silica gel column (9.5×17 cm) eluted with 2 L each of benzene, ethyl ether, ethyl acetate, and acetone.

The ethyl ether and ethyl acetate eluants were combined, evaporated to dryness and chromatographed on a second silica gel column (3.5×40 cm) packed in benzene and eluted with 150 ml of benzene, followed by a linear gradient elution from benzene to ethyl ether (156 17-ml fractions collected). This elution was followed by another linear gradient elution from ethyl ether to ethyl acetate (152 17-ml. fractions collected).

Dihydroxyaflavinine eluted in fractions 151-156 of the first gradient and fractions 1-45 of the second gradient. These fractions were combined and concentrated under vacuum, whereupon the product crystallized at 5° C. It was recrystallized from ethyl acetate; the mp was found to be 254°-256° C.

Example 2

Evaluation of Insecticidal Activity

Insects. Neonate larvae of *H. zea* and *S. frugiperda* were used for all assays. They were obtained from laboratory colonies reared on pinto bean-based diet at 27°±1° C., 40±10% relative humidity, and a 14:10 light:dark photoperiod.

The diet used to rear the insects was based on a standard pinto bean diet for many species of Lepidoptera which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. The tremorgenic mycotoxins were added in 125 $\mu$l of acetone or water to the liquid diet to give a final concentration of 25 ppm to 0.25 ppm. Upon addition of the tremorgen, the mixture was removed from the water bath. The chemicals were incorporated into the diets by blending vigorously with a vortex mixer for 20 sec. Preliminary observations with colored solutions of both water and acetone indicated uniform incorporation by this method. The diets were dispensed into culture plates, and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate *H. zea* or *S. frugiperda* larvae was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4, and 7 days, and the surviving larvae were weighed after 7 days. Each chemical set was tested on a total of 40 larvae.

Results of the evaluations are shown in Table I below.

It is understood that the foregoing detailed description is given merely by way of illustration and that modification and variations may be made therein without departing from the spirit and scope of the invention.

TABLE I

Toxicity of Tremorgenic Mycotoxins to *S. frugiperda* and *H. zea*

| Compound | *S. frugiperda* Mortality (%) | *S. frugiperda* 7 Day wt (% of control) | *H. zea* Mortality (%) | *H. zea* 7 Day wt (% of control) |
|---|---|---|---|---|
| | | 25 ppm | | |
| Penitrem A | 5.4 | 23.4 | 28.2 | 3.3 |
| Verruculogen | 5.0 | 20.0 | 0.0 | 20.2 |
| Dihydroxyaflavinine | 20.0 | 64.3 | 20.0 | 68.1 |
| Cytochalasin H | 8.1 | 42.4 | 2.6 | 87.5 |
| Paspaline | 0.0 | 79.7 | 0.0 | 73.8 |
| Paxilline | 10.0 | 71.1 | 2.7 | 64.2 |
| Chaetoglobosin C | 0.0 | 89.8 | 18.0 | 81.9 |
| Cyclopiazonic acid | 2.9 | 86.1 | 0.0 | 52.4 |
| | | 2.5 ppm | | |
| Penitrem A | 5.0 | 67.9 | 15.0 | 4.5 |
| Verruculogen | 0.0 | 80.2 | 7.5 | 77.4 |
| Dihydroxyaflavinine | 0.0 | 84.9 | 2.8 | 100.0 |
| | | 0.25 ppm | | |
| Penitrem A | 15.0 | 79.4 | 20.5 | 18.1 |

Some losses of insect occurred, and mortality values have been adjusted accordingly. Weights are based on survivors of mortality studies.

We claim:

1. A method of controlling agronomically important insects comprising applying to a locus of said insects an insecticidally effective amount of a fungal tremorgenic metabolite containing an indole moiety, wherein said metabolite is not cyclopiazonic acid.

2. The method as described in claim 1 wherein said tremorgenic metabolite is penitrem.

3. The method as described in claim 1 wherein said tremorgenic metabolite is verruculogen.

4. The method as described in claim 1 wherein said tremorgenic metabolite is dihydroxyaflavinine.

5. The method as described in claim 1 wherein said tremorgenic metabolite is cytochalasin.

6. The method as described in claim 1 wherein said tremorgenic metabolite is paspaline.

7. The method as described in claim 1 wherein said tremorgenic metabolite is paxilline.

8. The method as described in claim 1 wherein said tremorgenic metabolite is chaetoglobosin.

9. The method as described in claim 1 wherein said insects are Lepidoptera species.

10. The method as described in claim 1 wherein said insects are *Spodoptera frugiperda.*

11. The method as described in claim 1 wherein said insects are *Heliothis zea.*

12. The method as described in claim 2 wherein said penitrem is penitrem A.

* * * * *